United States Patent
Kobayashi et al.

(10) Patent No.: US 6,887,494 B2
(45) Date of Patent: May 3, 2005

(54) PIGMENTS AND EXTENDER PIGMENTS WITH ENHANCED SKIN ADHESION FOR COSMETIC PREPARATIONS

(75) Inventors: Masaru Kobayashi, Woodstock, CT (US); William Zavadoski, Madison, CT (US); William Kalriess, Tolland, CT (US); Ian Smith, Danielson, CT (US); Shigeru Kishida, Starrs, CT (US)

(73) Assignee: US Cosmetics, Dayville, CT (US)

( * ) Notice: Subject to any disclaimer, the term of this patent is extended or adjusted under 35 U.S.C. 154(b) by 35 days.

(21) Appl. No.: 09/850,534

(22) Filed: May 7, 2001

(65) Prior Publication Data

US 2002/0039562 A1 Apr. 4, 2002

Related U.S. Application Data

(63) Continuation of application No. 09/166,108, filed on Oct. 2, 1998, now abandoned.

(51) Int. Cl.[7] ............................. A61K 9/16; A61K 9/14; A61K 6/00; A61K 7/00
(52) U.S. Cl. ...................... 424/498; 424/490; 424/489; 424/401
(58) Field of Search ................. 424/498, 490, 424/489, 401, 63, 64, 59, 70.2

(56) References Cited

U.S. PATENT DOCUMENTS

| | | | | |
|---|---|---|---|---|
| 4,390,524 A | * | 6/1983 | Nasuno et al. | 424/70.14 |
| 4,578,266 A | * | 3/1986 | Tietjen et al. | 424/63 |
| 4,622,074 A | * | 11/1986 | Miyoshi et al. | 106/417 |
| 4,832,944 A | * | 5/1989 | Socci et al. | 106/414 |
| 5,073,364 A | * | 12/1991 | Giezendanner et al. | 132/294 |
| 5,486,233 A | * | 1/1996 | Mitchell et al. | 106/414 |
| 5,866,158 A | * | 2/1999 | Ribier et al. | 424/401 |
| 6,235,297 B1 | * | 5/2001 | Antonelli et al. | |

* cited by examiner

*Primary Examiner*—Thurman K. Page
*Assistant Examiner*—Isis Ghali
(74) *Attorney, Agent, or Firm*—Greenberg Traurig LLP; Eugene C. Rzucidlo

(57) ABSTRACT

A composition and method for enhancing skin adhesion of cosmetics by using pigments and extender pigments for the cosmetics, which pigments and extender pigments are treated with at least one hydrophobidizing agent and/or hydrophobidizing/lipophobidizing agent and one or more high viscosity esters having a viscosity in excess of 30 cps. The present invention further comprises such coated pigments and extender pigments as well as cosmetics made therewith.

8 Claims, No Drawings

PIGMENTS AND EXTENDER PIGMENTS WITH ENHANCED SKIN ADHESION FOR COSMETIC PREPARATIONS

CROSS REFERENCE TO RELATED UNITED STATES APPLICATIONS

This application is a continuation of U.S. patent application Ser. No. 09/166,108, "PIGMENTS AND EXTENDER PIGMENTS WITH ENHANCED SKIN ADHESION FOR COSMETIC PRODUCTS", filed on Oct. 2, 1998 by Kobayashi, et al., now abandoned, the contents of which are incorporated herein by reference.

FIELD OF THE INVENTION

The present invention relates to pigments and extender pigments and cosmetic preparations made therewith, and in particular to pigments and extender pigments with enhanced skin adhesion and spreadability.

BACKGROUND OF THE PRIOR ART

Make-up cosmetics, such as powder foundation, rouge, eye shadow, and lipstick, are commonly prepared with main constituents, such as pigments, extender pigments, binders, and other additives and are used to enhance attractiveness and to improve self-esteem.

However, conventional cosmetics do not last for extended periods when applied to the skin. Applied cosmetics, over time, tend to unevenly spot, change color, and even come off a skin surface primarily because of their interaction with sebum and perspiration with loss of adhesion. The extent of such degradation of applied cosmetics is dependent upon individual skin type, as well as ambient environmental factors such as humidity and temperature.

In the past, in order to prevent degradation of cosmetic make-up resulting from perspiration and in order to improve the wear and long-lasting characteristics thereof, the surface of pigments and extender pigments, used in the cosmetics were coated with silicone or metal soap to render such materials hydrophobic ("hydrophobidization"). While use of the hydrophobidized pigments and extender pigments reduced color drift resulting from interaction with perspiration, wear and long-lasting characteristics were not effectively improved since the hydrophobized cosmetics lacked effective skin adhesion.

Surface-coating on pigments and extender pigments with amino acid compounds, lecithin, and other similar materials has been suggested to improve longevity. However, while these surface-treatments improve the hydrophobicity and tactile feel of pigments, wear and long-lasting characteristics could not be effectively improved because of lack of adhesion to the skin.

Surface-coating with fluorocompounds has been also suggested since it provides both hydrophobicity and lipophobicity to pigments and extender pigments, whereby color drift due to perspiration and sebum is reduced. Again however, they did not improve wear and long-lasting characteristics since they did not improve adhesion to the skin.

Use of additives, such as animal oils (squalene and lanoline), fatty acids (myristic acid and stearic acid) and their esters, and glyceride of saturated fatty acids, to cosmetic preparations has been also suggested to improve wear. However, these additives are not easily dispersed on the surface of pigments to form uniform coating as they tend to agglomerate. Though these additives slightly improve tactile feel and adhesion to the skin nevertheless they are not very effective in improving the hydrophobicity, and wear and long-lasting characteristics.

SUMMARY OF THE INVENTION

It is accordingly an objective of the present invention to provide pigments and extender pigments which are characterized by smooth feel, good adhesion to the skin, minimal color drift in the presence of perspiration and sebum, good wear, and which are long-lasting, and to provide cosmetic preparations with similar good wear and long lasting characteristics. The present invention further includes the method used in providing such pigments and extender pigments.

Generally the present invention comprises a method for enhancing skin adhesion of cosmetics by using pigments and extender pigments for the cosmetics, which pigments and extender pigments are treated with at least one hydrophobidizing agent and/or hydrophobidizing/lipophobidizing agent and one or more high viscosity esters having a viscosity in excess of 30 cps. The present invention further comprises such coated pigments and extender pigments as well as cosmetics made therewith.

The resultant pigment and extender pigments have minimal color drift due to perspiration and improved adhesiveness with enhanced wear and long-lasting characteristics. Make-up cosmetic preparations comprised of the treated pigments and extender pigments exhibit improved characteristics, when applied to skin, including minimal color drift, longer wear, and minimal degradation even after extended periods of time.

According to the present invention, coating of a pigment or extender pigment with one or more hydrophobidizing or hydrophobidizing/lipophobidizing agents and one or more esters imparts hydrophobicity, smooth feel, improved adhesion to the skin, and is free from agglomeration because of uniform coating on each pigment or extender pigment. The pigment or extender pigment of the present invention is stable (i.e., the coating does not come off from the surface of the pigment) in cosmetic formulations and provides minimal color drift and improved adhesiveness, wear and long-lasting characteristics.

The high viscosity esters used in the present invention may be a single ester or a mixture of more than one ester or polyester made from fatty acids, such as stearic acid, isostearic acid, hydroxystearic acid, palmitic acid, oleic acid, erucic acid, ricinoleic acid, and myristic acid, and other carboxylic acids, such as malic acid, caprylic acid, capric acid, adipic acid, and 2-ethylhexanoic acid, and alcohol, such as glycerin, cholesterol, phytosterol, isostearyl alcohol, and octyldodecanol, and other organic compound, such as dimer of pentaerythritol and hexitol anhydrides derived from sorbitol.

Other objects, features and advantages of the present invention will become more evident from the following discussion and examples and comparative examples illustrating the efficacy of the present invention.

DETAILED DESCRIPTION OF THE INVENTION

Specific examples of esters useful in the present invention include: dipentaerythrityl hexahydroxystearate; hexaester of stearic acid and a dimer of pentaerythritol; diisostearyl malate; diester of isostearyl alcohol and malic acid; polyglyceryl triisostearate; ester of isostearic acid and glycerin; sorbitan; mixture of mono and diesters of oleic acid, stearic acid and hexitol anhydrides derived from sorbitol cholesteryl hydroxystearate; ester of cholesterol and hydroxystearic acid; mixed triester of glycerin with caprylic, capric, myristic and stearic acids; phytosteryl hydroxystearate; monoester of phytoterol and 12-hydroxystearic acid and other components (phytosterol and oligo (poly) ester); glyceryl octanoate/stearate/adipate; ester of glycerin and a blend of 2-ethylhexanoic acid, stearic acid, and adipic acid; octyldodecyl myristate (MOD); ester of octyldodecanol and myristic acid; octyldodecyl oleate (OOD); ester of octyldodecanol and oleic acid; octyldodecyl erucate (EOD); ester of octyldodecanol and erucic acid; octyldodecyl ricinoleate (ROD); ester of octyldodecanol and ricinoleic acid octyldodecyl isostearate (ISOD); ester of octyldodecanol and isostearic acid.

Specific low viscosity esters (less than 30 centipoises) esters which have not exhibited efficacy with respect to enhancement of skin adhesion include:
hydrogenated polyisobutene; and polytriglyceryl erucate/ eliostearate, isononyl isononanoate, neopentyl glycol dioctanoate, as well as complex ester/polymers.

In accordance with the present invention the esters should preferably be used in an amount of 0.1~30 wt %, and more preferably 1~5%, of the pigment or extender pigment to be treated, depending on the particle size and specific surface area of the pigment or extender pigment.

The hydrophobidizing agents used in the treated pigments and pigment extenders of the present invention include (but are not limited to) silicone oil, methylhydrogenpolysiloxane, dimethylsilicone, silane coupling agents, fatty acids, metal soap, acylamino acid salt, lecithin, acylpeptide salt and other known agents commonly used for cosmetics. These may be used by themselves or with combination with others. The hydrophobidizing agents may be applied to the pigment or extender pigment prior to coating with esters or simultaneously with esters.

The hydrophobidizing agents should be used in an amount of 0.1~30 wt %, and preferably 1~5%, of the pigment or extender pigment to be treated, depending on particle size and specific surface area.

In a preferred embodiment the hydrophobidizing/ lipophobidizing agents include DEA-C8-18 Perfluoroalkylethyl phosphate and its metal salt, fluorocompound of perfluoroalkylsilane and other known cosmetic agents. These may be used by themselves or in combination with other cosmetic agents. The hydrophobidizing/ lipophobidizing agents may be applied to the pigment or extender pigment prior to coating with esters or simultaneously with the esters.

The hydrophobidizing/lipophobidizing agents should be used in an amount of 0.1~30 wt %, and preferably 2~10%, of the pigment or extender pigment to be treated, depending on particle size and specific surface area.

The pigments and extender pigments used in the present invention includes (but is not limited to) inorganic pigments such as titanium dioxide, zinc oxide, zirconium oxide, yellow iron oxide, black iron oxide, red iron oxide, ultramarine, Prussian blue, chromium oxide, and chromium hydroxide); iridescent pigments (such as titanium mica and bismuth oxychloride); organic dyestuffs (such as tar dyestuffs and natural dyestuffs); and powder (such as silica beads, plastic (nylon or polyacryl) beads, talc, kaolin, white mica, sericite, other micas, magnesium carbonate, calcium carbonate, aluminum silicate, magnesium silicate, calcium silicate, clay and the like).

The most preferred materials are fine particles or superfine particles (smaller than 1 $\mu$m in diameter) of titanium oxide and color pigments (such as yellow iron oxide, black iron oxide, red iron oxide, ultramarine, Prussian blue, chromium oxide, chromium hydroxide, tar dyestuffs and the like), since they exhibit superior adhesion and spreadability.

The pigments and pigment extenders of the present invention are produced by mixing at least one ester, an organic solvent in which the ester is soluble, and a pigment or extender pigment, and drying the mixture by heating. The appropriate organic solvent should be selected in consideration of its flash point and ignition point and the surface activity of the pigment or extender pigment for surface treatment. Preferred examples of organic solvents include ethers, ketones, halogenated hydrocarbons, aliphatic hydrocarbons, and alcohols and mixture thereof or with other solvents such as water. The organic solvent is preferably used in an amount of 1~50 wt % relative to the pigment or extender pigment. The ester(s) should be heated to lower the viscosity to provide uniform coating on the pigment or extender pigment. Mixing of the ester(s), organic solvent, and pigment or extender pigment is preferably effected by simple mixture in an ordinary mixer. Alternatively, a mixture of ester(s) and the organic solvent is sprayed onto the pigment or extender pigment. Pigment or extender pigment may be coated with hydrophobidizing agents or hydrophobidizing/lipophobidizing agents prior to the ester-coating, or hydrophobidizing or phdrophobidizing/ lipophobidizing agents may be mixed with ester(s) for simultaneous coating. The heating of the mixture should be carried out in consideration of the heat resistance of the pigment or extender pigment and the vaporization and flammability characteristics of the organic solvent used.

EXAMPLES

The invention will be described in more detail with reference to the following examples and comparative examples.

Example 1

A test sample was made comprising 100 g of talc, 8 g of benzene, 1 g of dipentaerythrityl hexahydroxystearate, 1 g of octyldodecyl myristate, and 1.5 g of methylhydrogen polysiloxane which were mixed with each other for 5 minutes using a home mixer. The mixture was dried at 80° C. to remove benzene completely and then heated at 115° C. for 3 hours. The resultant pigment exhibited a smooth feel, good hydrophobicity and good skin adhesion.

Comparative Example 1

The same procedure as in Example 1 was repeated but without dipentaerythrityl hexahydroxystearate and octyldodecyl myristate. The resulting treated pigment was poor in adhesion notwithstanding its smooth feel and good hydrophobicity.

Example 2

A test sample was made comprising 100 g of red iron oxide, 10 g of methyl ethyl ketone, 2 g of polyglyceryl triisostearate, 1 g of octyldodecyl oleate, and 5 g of dimethylpolysiloxane chloride mixed with each other for 5 minutes using a home mixer. The mixture was dried at 80° C. to remove methyl ethyl ketone completely and then heated at 115° C. for 3 hours. A treated pigment was obtained having a good hydrophobicity and good adhesion.

Comparative Example 2

The same procedure as in Example 2 was repeated without dimethylpolysiloxane chloride. The resulting treated pigment had good adhesion to the skin but was poor in hydrophobicity, and color drift, in the presence of perspiration, was observed.

Example 3

A test sample of 100 g of titanium dioxide was dispersed in 500 ml of water. Ten grams of DEA-C8-18 perfluoroalkylethyl phosphate were added thereto and the combination was mixed. The pH of the mixture was adjusted to approximately 4 by dropwise addition of 1 N sulfuric acid aqueous solution with mixture thereafter for one hour. A resultant suspension was concentrated by dehydration by means of vacuum filteration to produce a moist paste-like cake. Three grams of diisostearyl malate, dispersed in 15 ml of methyl ethyl ketone, were added to the paste-like cake and mixed. The mixture was dried at 80° C. to completely remove methyl ethyl ketone and then heated at 105° C. for 3 hours. The treated pigment obtained exhibited good hydrophobicity and lipophobicity as well as good skin adhesion.

Comparative Example 3

A test sample comprising 100 g of titanium dioxide was dispersed in 500 ml of water. To this, 10 g of DEA-C8-18 perfluoroalkylethyl phosphate was added and the mixed. The pH of the mixture was adjusted to approximately 4 by dropwise addition of 1 N sulfuric acid aqueous solution and mixing was carried out for one hour. The suspension thus obtained was concentrated through dehydration by means of vacuum filteration to produce a moist paste-like cake containing. The paste-like cake was then dried at 105° C. for 5 hours. The treated pigment obtained had good hydrophobicity and lipiphobicity but was poor in adhesion to the skin.

Example 4

A powder foundation of the following formulation was prepared with the following components in the weight percentages given.

| Component 1 | |
| --- | --- |
| Talc | 39.0% |
| Sericite | 25.0% |
| Mica | 20.0% |
| Titanium dioxide | 7.0% |
| Titanium dioxide (fine particle) | 5.0% |
| Yellow iron oxide | 3.3% |
| Black iron oxide | 0.2% |
| Red iron oxide | 0.5% |
| Component 2 (wt % relative to Component 1) | |
| Liquid paraffin | 5.0% |
| Stearyl alcohol | 3.0% |
| Beeswax | 3.0% |
| Squalene | 1.0% |

Component 1, a mixture of pigments and extender pigments, was mixed well. 1.5 g of dipentaerythrityl hexahydroxystearate, 1.5 g of octyldodecyl myristate and 5% of dimethylpolysiloxane chloride dispersed in 10% of methyl ethyl ketone were added to the component 1 and mixed for 5 minutes using a mixer. The mixture was dried at 80° C. to remove methyl ethyl ketone completely and then heated at 115° C. for 3 hours. After this was atomized, component 2 (which was previously heated) was added and mixed using a Henschel mixer and atomized using an atomizer. This was filled into a cosmetic container to form a desired product (powder foundation).

Comparative Example 4

Component 1 of Example 4 was mixed well. 5% of dimethylpolysiloxane chloride dispersed in 10% of methyl ethyl ketone was added to the component 1 and mixed for 5 minutes using a mixer. The mixture was dried at 80° C. to remove methyl ethyl ketone completely and then heated at 115° C. for 3 hours. After this was atomized, component 2 (which has been heated) was added and mixed using a Henschel mixer and atomized using an atomizer. This was filled into a cosmetic container to form a desired product (powder foundation).

Comparative Example 5

Component 1 of Example 4 was mixed well. 1.5 g of dipentaerythrityl hexahydroxystearate, 1.5 g of octyldodecyl myristate dispersed in 10% of methyl ethyl ketone were added to the component 1 and mixed for 5 minutes using a mixer. The mixture was dried at 80° C. to remove methyl ethyl ketone completely and then heated at 115° C. for 3 hours. After this was atomized, component 2 (which was previously heated) was added and mixed using a Henschel mixer and atomized using an atomizer. This was filled into a cosmetic container to form a desired product (powder foundation).

The samples of powder foundation obtained in Example 4 and Comparative Examples 4 and 5 were tested for spreadability, adhesion, color stability (absence of color drift and color saturation), and water repellency by 20 female subjects. The results are shown in Table 1. The criteria for the rating are as follows:

5: very good
4: slightly good
3: mediocre
2: slightly poor
1: very poor

TABLE 1

| Sample | spreadability | adhesion | color stability | water repellency |
| --- | --- | --- | --- | --- |
| Example 4 | 3 | 5 | 4 | 5 |
| Comparative Ex 4 | 3 | 2 | 3 | 5 |
| Comparative Ex 5 | 2 | 4 | 1 | 1 |

From the above it is evident that the powder foundation made in Example 4 (present invention) is superior to those made in Comparative Examples 4 and 5 in spreadability, adhesion, color stability (absence of color drift and color saturation), and water repellency.

Example 5

A liquid foundation of the following formulation was prepared.

| Component A | |
| --- | --- |
| Cyclomethicone | 12.0% |
| Emulsified volatile oil | 2.0 |
| Titanium dioxide | 9.0 |
| Red iron oxide | 0.7 |
| Yellow iron oxide | 0.2 |
| Black iron oxide | 3.0 |
| Talc | 2.0 |

-continued

| Component B | |
|---|---|
| Propylparaben | 0.2 |
| Polyoxyethylene lauryl ether | 0.5 |
| Component C | |
| Emulsified volatile oil | 18.0 |
| Dimethylsilicone (50 cs) | 3.0 |
| Tocopherol acetate | 0.1 |
| Corn oil | 0.05 |
| Component D | |
| Methylparaben | 0.2 |
| Propylene glycol | 8.0 |
| Component E | |
| Sodium dehydroacetate | 0.3 |
| Pantothenyl alcohol | 0.2 |
| Sodium chloride | 2.0 |
| Purified water | (remainder) |

Initially, component A, a mixture of pigments and extender pigments, was surface-treated with DEA-C8-18 perfluoroalkylethyl phosphate 3%, 1% of dipentaerythrityl hexahydroxystearate and 1% of octyldodecyl myristate in the same manner as in Example 3. Component A was mixed with Components B and C, which had been melted by heating at 60° C. Components D and E were mixed with each other after melting by heating at 60° C. The second mix was slowly added to the first mix with stirring to effect emulsification. A sample of liquid foundation upon cooling.

Comparative Example 6

The same procedure as in Example 5 was used to prepare a sample of liquid foundation, except that the dipentaerythrityl hexahydroxystearate and octyldodecyl myristate were not used,.

The samples of liquid foundation obtained in Example 5 and Comparative Example 6 were tested for spreadability, adhesion, and color stability by 20 female subjects. The results are shown in Table 2. The criteria for the rating are as follows:

5: very good
4: slightly good
3: mediocre
2: slightly poor
1: very poor

TABLE 2

| Sample | spreadability | adhesion | color stability |
|---|---|---|---|
| Example 5 | 4 | 5 | 4 |
| Comp. Ex. 6 | 4 | 3 | 3 |

It is evident that liquid foundation made in Example 5 (present invention) is superior to that of Comparative Example 6 in adhesion, and color stability.

Example 6

A lipstick of the following formulation was prepared.

| Castor oil | 57.9% |
|---|---|
| Candelilla wax | 6.0 |

-continued

| Carnauba wax | 4.0 |
|---|---|
| Beeswax | 8.0 |
| Isopropyl myristate | 12.0 |
| Propylparaben | 0.1 |
| Titanium dioxide | 9.0 |
| D&C red No. 7 (calcium lake) | 3.0 |

Titanium dioxide and D&C red No. 7 calcium lake were mixed with 9% (with respect to the amount of titanium dioxide and D&C red No. 7 calcium lake) of benzene, 3.5% of sorbitan sesquioleate and 4% of methylhydrogen polysiloxane for 5 minutes using a home mixer. The mixture was dried at 80° C. to remove benzene completely and then heated at 115° C. for 3 hours. The surface treated pigments were mixed with 30% of castor oil and the mixture was further dispersed by a three roller mill. The rest of the components were heated at 85° C. and mixed until completely melted. The melt was cooled to 80° C. and the pigment mixture was poured into and mixed until uniform. The mixture was poured into molds while maintaining the temperature at 70~75° C.

Comparative Example 7

The same procedure as in Example 6, except that the sorbitan sesquioleate was not used, was repeated to prepare a sample of lipstick. Lipstick made in Example 6 was superior to that of Comparative Example 7 in spreadability, adhesiveness, wear and long-lasting characteristics.

It is understood that the above examples demonstrating the efficacy of the present invention are merely illustrative of the present invention and that other materials and combinations are similarly efficacious and within the scope of the present invention as defined in the following claims.

What is claimed is:

1. A composition for use in a cosmetic preparation comprising at least one of a pigment and extender pigment having exposed surfaces thereof, wherein the surfaces of the pigment and extender pigment art coated with at least one of a hydrophobidizing agent and a hydrophobidizing/lipophobidizing agent and at least one high viscosity ester of viscosity in excess of 30 cps, wherein the ester can be either a smile ester or a mixture of more than one ester or polyester, wherein these esters or polyesters are made from fatty acids selected from the group consisting of stearic acid, isostearic acid, hydroxystearic acid, palmitic acid, oleic acid, erucic acid, ricinoleic acid, and myristic acid and from carboxylic acids selected from the group consisting of malic acid, caprylic acid, capric acid, adipic acid, and 2-ethylhexanoic acid; an alcohol selected from the group consisting of glycerin, cholesterol, phytosterol, isostearyl alcohol, and octyldodecanol, and organic compounds selected from the group consisting of a dimer of pentaerythritol and hexitol anhydrides derived from sorbitol whereby skin adhesion is enhanced and wherein said coating is stable even in the presence of water.

2. A cosmetic preparation made with the composition of claim 1.

3. The composition of claim 1, wherein the ester is selected from dipentaerthrityl hexahydroxystearate, hexaester of stearic acid and a dimer of pentacrythritol; diistearyl malate; diester of isostearyl alcohol and malic acid; polyglyceryl triistearate; ester of isostearic acid and glycerin; sorbitan sesquioleate; mixture of mono- and diesters of oleic acid, stearic acid, and hexitol anhydrides derived from sorbitol cholesteryl hydroxystearate; ester of cholesterol and hydroxystearic acid; mixed triester of glycerin with caprylic, capric, myristic, and stearic acids; phytosteryl hydroxystearate; monoester of phytosterol and 12-hydroxystearic acid and phytosterol and oligo (poly) ester; glyceyl octanoate/stearate/adipate; ester of glycerin and a blend of 2-ethylhexanoic acid, stearic acid, and adipic acid; octyldodecyl myristate (MOD); ester of octyldodecanol and myristic acid; octyldodecyl oleate (OOD); ester of octyldodecanol and oleic acid; octyldodecyl erucate (EOD); ester of octyldodocanol and erucic acid; octyldodecyl ricinoleate (ROD); ester of octyldodecanol and ricinolelc acid; octyldodecyl isostearate (ISOD); and ester of octyldodecanol and isostearic acid.

4. The composition of claim 3, wherein the hydrophobidizing agent is a member of the group consisting of silicone oil, methylhydrogenpolysiloxane, dimethylsilicone, silane coupling agents, fatty acids, metal soap, acylamino acid salt, lecithin, and acylpeptide salt.

5. The composition of claim 1, wherein the hydrophobidizing/lipophobidizing agent is selected from the group consisting of DEA-C8-18 perfluoroalkylethyl phosphate and its metal salt, and fluorocompound of perfluoroalkylsilane.

6. The composition of claim 1, wherein the pigments and extender pigments are selected from the group consisting of inorganic pigments, titanium dioxide, zinc oxide, zirconium oxide, yellow iron oxide, black iron oxide, red iron oxide, ultramarine, Prussian blue, chromium oxide, and chromium hydroxide, iridescent pigments, titanium mica and bismuth oxychloride; organic dyestuffs, tar dyestuffs, and natural dyestuffs; silica beads, plastic nylon and/or polyacryl beads, talc, kaolin, white mica, sericite, micas, magnesium carbonate, calcium carbonate, aluminum silicate, magnesium silicate, calcium silicate, and clay.

7. The composition of claim 6, wherein the pigments and extender pigments are selected from fine particles and superfime particles of titanium oxide and color pigments, yellow iron oxide, black iron oxide, red iron oxide, ultramarine, Prussian blue, chromium oxide, chromium hydroxide, and tar dyestuffs, wherein said fine and superfime particles are less than 1$\mu$m in diameter.

8. A method for increasing skin adhesion of cosmetic preparations having pigments or extender pigments, comprising the steps of:

a) coating surfaces of the pigments or extender pigments with at least one of a hydrophobidizing agent, and a hydrophobidizing/lipophobidizing agent and at least one high viscosity ester of viscosity in excess of 30 cps, wherein the ester can be either a single ester or a mixture of more than one ester or polyester, wherein these esters or polyesters are made from fatty acids selected from the group consisting of stearic acid, isostearic acid, hydroxystearic acid, palmitic acid, oleic acid, erucic acid, ricinoleic acid, and myristic acid and from carboxylic acids selected from the group consisting of malic acid, caprylic acid, capric acid, adipic acid, and 2-ethylhexanoic acid; an alcohol selected from the group consisting of glycerin, cholesterol, phytosterol, isostearyl alcohol, and octyldodecanol, and organic compounds selected from the group consisting of a dimer of pentaerythritol and hexitol anhydrides derived from sorbitol said coating being stable in the presence of water, and b) incorporating the pigment or extender pigment in a cosmetic preparation.

* * * * *